United States Patent
Patel et al.

(10) Patent No.: US 10,111,652 B2
(45) Date of Patent: Oct. 30, 2018

(54) TWO-PIECE KNOTLESS SUTURE ANCHOR

(71) Applicant: Smith & Nephew, Inc., Memphis, TN (US)

(72) Inventors: Nehal Navinbhai Patel, Boston, MA (US); Matthew Edwin Koski, Westford, MA (US); Geoffrey Ian Karasic, Milton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 141 days.

(21) Appl. No.: 15/118,224

(22) PCT Filed: Mar. 6, 2015

(86) PCT No.: PCT/US2015/019175
§ 371 (c)(1),
(2) Date: Aug. 11, 2016

(87) PCT Pub. No.: WO2015/134872
PCT Pub. Date: Sep. 11, 2015

(65) Prior Publication Data
US 2017/0172560 A1    Jun. 22, 2017

Related U.S. Application Data

(60) Provisional application No. 61/948,929, filed on Mar. 6, 2014.

(51) Int. Cl.
*A61B 17/04*    (2006.01)

(52) U.S. Cl.
CPC .... *A61B 17/0401* (2013.01); *A61B 2017/042* (2013.01); *A61B 2017/044* (2013.01);
(Continued)

(58) Field of Classification Search
CPC .......... A61B 17/0401; A61B 2017/042; A61B 2017/0414; A61B 2017/044
See application file for complete search history.

(56) References Cited

U.S. PATENT DOCUMENTS 5,207,679 A    5/1993  Li
5,224,946 A    7/1993  Hayhurst et al.
(Continued)

FOREIGN PATENT DOCUMENTS

EP    1199035 A1    4/2002

OTHER PUBLICATIONS

BioComposite PushLock, downloaded from www.devicinnovation.com, Feb. 16, 2014.
(Continued)

*Primary Examiner* — Son Dang
(74) *Attorney, Agent, or Firm* — Burns & Levinson, LLP; Joseph M. Maraia (57) ABSTRACT

A suture anchor assembly includes a suture anchor and a suture anchor inserter. The anchor includes a flexible distal tip and a rigid proximal anchor body. The distal tip includes a transverse suture eyelet and a cavity formed in a proximal end of the tip. The anchor body includes a lumen extending between proximal and distal ends of the body. The anchor inserter includes a tubular outer shaft and an inner inserter slidably received therein. The anchor assembly is actuatable to move the anchor tip and inner shaft proximally while the outer shaft and anchor body remain in place, urging the proximal end of the anchor tip against the distal end of the anchor body. The proximal end of the tip is deformable to accommodate at least a portion of the distal end of the anchor body within the anchor tip cavity.

10 Claims, 5 Drawing Sheets

(52) U.S. Cl.
CPC .............. *A61B 2017/0409* (2013.01); *A61B 2017/0412* (2013.01); *A61B 2017/0414* (2013.01); *A61B 2017/0424* (2013.01); *A61B 2017/0425* (2013.01)

(56) References Cited

U.S. PATENT DOCUMENTS

| | | | |
|---|---|---|---|
| 5,268,001 A * | 12/1993 | Nicholson | A61B 17/0401 606/104 |
| 5,354,298 A | 10/1994 | Lee et al. | |
| 5,472,452 A * | 12/1995 | Trott | A61B 17/0401 24/297 |
| 5,618,314 A | 4/1997 | Harwin et al. | |
| 5,643,321 A * | 7/1997 | McDevitt | A61B 17/0401 606/232 |
| 5,702,215 A * | 12/1997 | Li | F16B 13/0866 411/21 |
| 5,935,129 A | 8/1999 | McDevitt et al. | |
| 5,957,953 A * | 9/1999 | DiPoto | A61B 17/0401 606/232 |
| 5,980,558 A | 11/1999 | Wiley | |
| 5,993,459 A * | 11/1999 | Larsen | A61B 17/0469 606/104 |
| 6,149,669 A * | 11/2000 | Li | A61B 17/0401 606/232 |
| 6,641,597 B2 | 11/2003 | Burkhart et al. | |
| 6,692,516 B2 | 2/2004 | West, Jr. et al. | |
| 6,932,834 B2 * | 8/2005 | Lizardi | A61B 17/0401 606/228 |
| 7,008,451 B2 * | 3/2006 | Justin | A61F 2/0811 623/13.14 |
| 7,517,357 B2 * | 4/2009 | Abrams | A61B 17/0401 606/232 |
| 7,678,134 B2 | 3/2010 | Schmieding et al. | |
| 7,780,701 B1 * | 8/2010 | Meridew | A61B 17/0401 606/139 |
| 7,867,251 B2 * | 1/2011 | Colleran | A61B 17/0401 606/232 |
| 7,867,264 B2 * | 1/2011 | McDevitt | A61B 17/0401 606/313 |
| 8,162,978 B2 * | 4/2012 | Lombardo | A61B 17/0401 606/232 |
| 8,372,124 B2 * | 2/2013 | Paulk | A61B 17/0401 606/300 |
| 8,430,909 B2 | 4/2013 | Dreyfuss | |
| 8,523,902 B2 * | 9/2013 | Heaven | A61B 17/0401 606/232 |
| 8,545,535 B2 * | 10/2013 | Hirotsuka | A61B 17/0401 606/232 |
| 8,545,536 B2 | 10/2013 | Mayer et al. | |
| 8,956,395 B2 * | 2/2015 | Graf | A61B 17/8869 606/321 |
| 9,308,035 B2 * | 4/2016 | Biedermann | A61B 17/7258 |
| 9,572,563 B2 * | 2/2017 | Berelsman | A61B 17/0401 |
| 9,636,143 B2 * | 5/2017 | Weisbrod | A61B 17/0401 |
| 9,649,103 B2 * | 5/2017 | Arai | A61B 17/0401 |
| 9,775,597 B2 * | 10/2017 | Heaven | A61B 17/0401 |
| 2002/0147463 A1 * | 10/2002 | Martinek | A61B 17/0401 606/232 |
| 2006/0282081 A1 * | 12/2006 | Fanton | A61B 17/0401 606/232 |
| 2008/0208253 A1 | 8/2008 | Dreyfuss et al. | |
| 2009/0248068 A1 * | 10/2009 | Lombardo | A61B 17/0401 606/232 |
| 2009/0312794 A1 | 12/2009 | Nason et al. | |
| 2009/0318964 A1 * | 12/2009 | Lombardo | A61B 17/0401 606/232 |
| 2010/0121355 A1 * | 5/2010 | Gittings | A61B 17/0401 606/148 |
| 2011/0004242 A1 | 1/2011 | Stchur | |
| 2011/0118762 A1 | 5/2011 | Dooney, Jr. et al. | |
| 2013/0103080 A1 | 4/2013 | Hernandez | |
| 2013/0267998 A1 * | 10/2013 | Vijay | A61B 17/0401 606/232 |
| 2015/0282801 A1 * | 10/2015 | Arai | A61B 17/0401 606/232 |

OTHER PUBLICATIONS 2.5 mm PushLock® Knotless Suture Anchor—Arthrex, downloaded from www.arthrex.com (2013).
Knotless Suture Anchors, downloaded from www.arthrex.com on Feb. 16, 2014.
Y-Knot® Flex All-Suture Anchor System, downloaded from www.conmed.com (2013).
BIORAPTOR™ Knotless Suture Anchor, downloaded from www.endoinnovation.com (2010).
IPRP from related PCT Application No. PCT/US2015/019175 dated Sep. 6, 2016.

* cited by examiner

TWO-PIECE KNOTLESS SUTURE ANCHOR

CROSS REFERENCE TO RELATED APPLICATIONS

This application is the U.S. national phase entry under 35 U.S.C. § 371 of International Application No. PCT/US2015/019175, filed Mar. 6, 2015, entitled TWO-PIECE KNOTLESS SUTURE ANCHOR, which in turn claims priority to U.S. Provisional Patent Application No. 61/948,929, filed Mar. 6, 2014, the contents of which are incorporated herein by reference in their entirety for all purposes.

BACKGROUND

Suture anchors are employed in surgical repair operations for fixing a suture in a desired location with respect to a patient's anatomy. Typically, one or more sliding knots are formed in the suture in order to secure the suture to the anchor. However, tying of sliding knots can be difficult and/or time consuming, especially in combination with evolving arthroscopic surgical procedures. Accordingly, there is an ongoing demand for improved suture anchors and corresponding delivery systems that do not rely upon sliding suture knots to secure the suture to the anchor.

SUMMARY

In an embodiment, a suture anchor assembly is provided. The suture anchor assembly includes a suture anchor and an anchor inserter. The suture anchor includes an elongated anchor body having a lumen extending there-through between a proximal end and a distal end along a longitudinal axis. The suture anchor further includes an anchor tip having a proximal end and a distal end, the anchor tip including an eyelet extending transversely there-through and a cavity formed in the proximal end of the anchor tip, where the tip is separate from the anchor body. The anchor inserter includes a tubular outer shaft extending between a proximal end and a distal end. The anchor inserter further includes an inner shaft slidably receivable within the outer shaft and the anchor body lumen. The distal end of the inner shaft is mechanically engageable with the cavity of the anchor tip so as to position the anchor tip distally of the anchor body. The inner shaft is proximally retractable while mechanically engaged with the anchor tip so as to urge the proximal end of the anchor tip against the distal end of the anchor body. The proximal end of the anchor tip is deformable to accommodate receipt of at least a portion of the distal end of the anchor body within the cavity upon being urged proximally against the distal end of the anchor body.

Further embodiments of the suture anchor assembly may include one or more of the following, in any combination.

In an embodiment of the suture anchor, the proximal end of the anchor tip deforms radially outward to circumferentially overlie the portion of the distal end of the anchor body received within the cavity.

In an embodiment of the suture anchor assembly, the anchor tip further includes a plurality of slots extending distally from the proximal end of the anchor tip along the length of the cavity defining a plurality of wings, where the plurality of wings deflect outward to accommodate the portion of the distal end of the anchor body received within the cavity.

In an embodiment of the suture anchor assembly, the proximal end of the anchor tip does not extend into the anchor body lumen upon being urged proximally against the distal end of the anchor body.

In an embodiment of the suture anchor assembly, the cavity does not intersect the eyelet within the anchor tip.

In an embodiment of the suture anchor assembly, a diameter of the cavity at the proximal end of the anchor tip is less than a diameter of the distal end of the anchor body.

In an embodiment of the suture anchor assembly, the mechanical engagement between the distal end of the inner shaft and the cavity is a break-away connection.

In an embodiment, the suture anchor assembly further includes a first plurality of threads formed along an inner surface of the cavity and a second plurality of threads extending proximally from the distal end of the inner shaft, the second plurality of threads adapted to mate with the first plurality of threads. The first and second plurality of threads are disengageable from one another by stripping upon proximal retraction of the inner shaft with respect to the inner shaft by a distance sufficient to shear at least one of the first and second plurality of threads and allow the first and second plurality of threads to slip past one another.

In an embodiment, the suture anchor assembly further includes a suture extending through the eyelet.

In an embodiment of the suture anchor assembly, the inner shaft does not engage the suture.

In an embodiment, a method of suture fixation is provided. The method includes providing a suture anchor assembly including a suture anchor and an anchor inserter. The suture anchor includes an elongated anchor body having a lumen extending there-through between a proximal end and a distal end along a longitudinal axis. The suture anchor further includes an anchor tip having a proximal end and a distal end, the anchor tip including an eyelet extending transversely there-through and a cavity formed in the proximal end of the anchor tip, where the tip is separate from the anchor body. The anchor inserter includes a tubular outer shaft extending between a proximal end and a distal end. The anchor inserter further includes an inner shaft received within the outer shaft and the anchor body lumen. The distal end of the inner shaft is mechanically engaged with the cavity of the anchor tip so as to position the anchor tip distally of the anchor body. The method further includes routing a suture through the eyelet, inserting at least a portion of the anchor into a bone hole using the anchor inserter, and proximally retracting the inner shaft with respect to the anchor body and the outer shaft so as to urge the proximal end of the anchor tip against the distal end of the anchor body. The proximal end of the anchor tip is deformable to accommodate receipt of at least a portion of the distal end of the anchor body within the cavity upon being urged proximally against the distal end of the anchor body.

Further embodiments of the method may include one or more of the following, in any combination.

In an embodiment of the method, the proximal end of the anchor tip deforms radially outward to circumferentially overlie the portion of the distal end of the anchor body received within the cavity.

In an embodiment of the method, the anchor tip further includes a plurality of slots extending distally from the proximal end of the anchor tip along the length of the cavity defining a plurality of wings, where the plurality of wings deflect outward to accommodate the portion of the distal end of the anchor body received within the cavity.

In an embodiment, the method further includes disengaging the mechanical engagement of the inner shaft to the cavity after deformation of the anchor tip to accommodate the portion of the distal end of the anchor body received within the cavity.

In an embodiment of the method, the mechanical engagement between the distal end of the inner shaft and the cavity is a break-away connection and disengaging the mechanical engagement includes severing the break-away connection.

In an embodiment of the method, the inner shaft does not engage the suture.

In an embodiment of the method, the proximal end of the anchor tip does not extend into the anchor body lumen upon being urged proximally against the distal end of the anchor body.

In an embodiment, a suture anchor assembly is provided. The suture anchor assembly includes a suture anchor and an anchor inserter. The suture anchor includes an elongated anchor body having a lumen extending there-through between a proximal end and a distal end along a longitudinal axis, the anchor body further including a first pair of longitudinal channels formed on a surface of the lumen. The suture anchor also includes an anchor tip having a proximal end and a distal end, the anchor tip being separate from the anchor body. The anchor tip further includes an eyelet extending transversely there-through, a suture bridge extending transversely there-through, a cavity formed in the proximal end of the anchor tip, and a second pair of channels formed within the anchor tip, extending distally from the cavity and adjacent to the suture bridge. The anchor inserter includes a tubular outer shaft extending between a proximal end and a distal end and an inner shaft slidably receivable within the outer shaft and the anchor body lumen. The suture anchor assembly further includes a flexible member routed through the anchor assembly with the anchor tip positioned distally of the anchor body, where the flexible member bends around the suture bridge and free limbs of the flexible member extending from the bend are slidably received within a passageway formed by the first and second pair of channels. The flexible member is proximally retractable while routed through the anchor assembly so as to urge the proximal end of the anchor tip against the distal end of the anchor body. The proximal end of the anchor tip is deformable so as to accommodate receipt of at least a portion of the distal end of the anchor body within the cavity upon being urged proximally against the distal end of the anchor body.

Further embodiments of the suture anchor assembly may include one or more of the following, in any combination.

In an embodiment of the suture anchor assembly, the proximal end of the anchor tip deforms radially outward to circumferentially overlie the portion of the distal end of the anchor body received within the cavity.

In an embodiment of the suture anchor assembly, the eyelet defines a plurality of wings in the proximal end of the anchor tip and the plurality of wings deflect outward to accommodate the portion of the distal end of the anchor body received within the cavity.

In an embodiment of the suture anchor assembly, the suture bridge is positioned at the distal terminus of the anchor tip and the second pair of channels extend through the distal terminus of the anchor tip.

In an embodiment of the suture anchor assembly, the suture bridge is proximally distanced from the distal terminus of the anchor tip and the passageway further includes a transversely extending segment positioned distally of the suture bridge and intersecting the second pair of channels for routing the flexible member around the suture bridge within the anchor tip.

In an embodiment, a method of suture fixation is provided. The method includes providing a suture anchor assembly including a suture anchor and an anchor inserter. The suture anchor includes an elongated anchor body having a lumen extending there-through between a proximal end and a distal end along a longitudinal axis, the anchor body further including a first pair of longitudinal channels formed on a surface of the lumen. The suture anchor also includes an anchor tip having a proximal end and a distal end, the anchor tip being separate from the anchor body. The anchor tip includes an eyelet extending transversely there-through, a suture bridge extending transversely there-through, a cavity formed in the proximal end of the anchor tip, and a second pair of channels formed within the anchor tip, extending distally from the cavity and adjacent to the suture bridge. The anchor inserter includes a tubular outer shaft extending between a proximal end and a distal end and an inner shaft slidably received within the outer shaft and the anchor body lumen. The suture anchor assembly also includes a flexible member routed through the anchor assembly with the anchor tip positioned distally of the anchor body, where the flexible member bends around the suture bridge and free limbs of the flexible member extending from the bend are slidably received within a passageway formed by the first and second pair of channels. The method further includes routing a repair suture through the eyelet, inserting at least a portion of the anchor into a bone hole using the anchor inserter, and proximally retracting the inner shaft and the free limbs of the flexible member with respect to the anchor body and the outer shaft so as to urge the proximal end of the anchor tip against the distal end of the anchor body. The proximal end of the anchor tip is deformable so as to accommodate receipt of at least a portion of the distal end of the anchor body within the cavity upon being urged proximally against the distal end of the anchor body.

Further embodiments of the method may include one or more of the following, in any combination.

In an embodiment of the method, the proximal end of the anchor tip deforms radially outward to circumferentially overlie the portion of the distal end of the anchor body received within the cavity.

In an embodiment of the method, the eyelet defines a plurality of wings in the proximal end of the anchor tip and the plurality of wings deflect outward to accommodate the portion of the distal end of the anchor body received within the cavity.

In an embodiment, the method further includes removing the flexible member, the inner shaft, and the outer shaft from the anchor.

In an embodiment of the method, the suture bridge is positioned at the distal terminus of the anchor tip and the second pair of channels extend through the distal terminus of the anchor tip.

In an embodiment of the method, the suture bridge is proximally distanced from the distal terminus of the anchor tip and the passageway further includes a transversely extending segment positioned distally of the suture bridge and intersecting the second pair of channels for routing the flexible member around the suture bridge within the anchor tip.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

There are a number of challenges faced in delivery of suture anchor assemblies for use in soft tissue to bone repair. One such challenge is locating the point at which the suture anchor is to be inserted into the bone. Often, suture anchors are inserted into the bone within a previously prepared hole. While the general location of the bone hole is known, it can be difficult to maintain the bone hole precisely aligned with the delivery pathway of the anchor assembly given its relatively small size, as well as limited visibility within the surgical site. Accordingly, is desirable for a suture anchor assembly to possess the capability to locate a bone hole within a defined area in which the hole is known to be located.

Another such challenge is maintaining a clear delivery pathway for the suture anchor assembly to the bone hole. As the connections between the soft tissue and bone in the region of the repair are weakened or severed, soft tissue and bone can shift during surgery, blocking the delivery pathway, requiring a surgeon to move portions of the patient's anatomy. Accordingly, it is also desirable for a suture anchor assembly to support the mechanical forces (e.g., moments, axial forces, shear forces, etc.) experienced if a surgeon were to use the suture assembly to move soft tissue and/or bone.

Embodiments of the present disclosure describe suture anchors and corresponding suture anchor inserters (collectively suture anchor assemblies) that satisfy these requirements. Further embodiments of the disclosed suture anchor assemblies are employed without the use of suture knots. The disclosed suture anchor assemblies may be employed in surgical repair operations that include, but are not limited to, joint repair (e.g., shoulder joint, knee joint), bone block fusion (e.g., Latarjet), and the like, performed arthroscopically or non-arthroscopically.

In an embodiment, suture anchor assemblies are provided that include a suture anchor and a suture anchor inserter. The anchor includes a flexible distal tip and a rigid proximal anchor body. The distal tip includes a transverse suture eyelet and a cavity formed in a proximal end of the tip. The anchor body is fully cannulated, with a lumen extending between proximal and distal ends of the body. The anchor inserter includes a tubular outer shaft and an inner inserter slidably received therein.

The anchor is mounted to the anchor inserter for delivery to a repair site (e.g., a bone hole). For example, the inner shaft is received within the anchor body, with the proximal end of the anchor body adjacent to or contacting a distal end of the outer shaft. When the anchor is mounted to the anchor inserter, the anchor tip is also positioned distal to the anchor body, with a proximal end of the anchor tip adjacent to or contacting the distal end of the anchor body. Prior to insertion within a patient, a suture is further placed within the anchor tip eyelet.

In use, the anchor is inserted (e.g., pounded) into a bone hole using the anchor inserter. Each of the components of the anchor assembly are further constrained in place with respect to one another until after insertion is complete. Beneficially, the anchor assembly design provides a number of advantages that address the challenges noted above, facilitating anchor delivery. In one example, the anchor is supported by the inner shaft, providing mechanical durability that allows the surgeon to move soft tissue and/or bone with the anchor assembly. In another example, the anchor tip is useable by a surgeon as a probe to tactilely identify the location of the bone hole.

Once the anchor is inserted into the bone hole, the anchor assembly is actuated such that the anchor tip and inner shaft are proximally retracted while the outer shaft and anchor body remain in place, urging the proximal end of the anchor tip against the distal end of the anchor body. As the anchor tip is flexible, relative to the anchor body, this motion causes the proximal end of the tip to deform and accommodate at least a portion of the distal end of the anchor body within the anchor tip cavity. In addition to securing the anchor tip to the anchor body, this proximal activation of the suture anchor also results in lateral expansion of at least a portion of the anchor tip against the surrounding bone, further enhancing fixation of the anchor to the bone. After the anchor tip is proximal retracted by a desired distance, the anchor inserter is removed from the anchor, leaving the anchor and suture secured to the bone.

Embodiments of a first suture anchor assembly 100 will now be discussed with respect to FIGS. 1 and 2A-2B. The anchor assembly 100 includes an anchor 102 including an elongated anchor body 106 and an anchor tip 110, separate from the anchor body 106. The anchor assembly 100 further includes an anchor inserter 104 including an outer shaft 114 and an inner shaft 116. Each of the components of the anchor 102 and anchor inserter 104 is discussed in detail below.

With regards to the anchor 102, the anchor body 106 is generally tubular, including a lumen 106A extending along a longitudinal axis 112 between a proximal end and a distal end. In the embodiment of FIG. 1, the anchor body 106 further includes a plurality of tissue engaging features 120 (e.g., a plurality of annular ribs) formed on an outer surface of the anchor body 106 for aiding fixation of the anchor within bone. However, in alternative embodiments, the tissue engaging features may include one or more of barbs, protrusions, threads, and the like. In further embodiments, the tissue engaging features may be omitted.

The anchor tip 110 is formed as a separate component from the anchor body 106 and includes an internal cavity 110A and an eyelet 110B. The cavity 110A is formed within the proximal end of the anchor tip 110 and extends a selected distance distally there-from. As discussed in greater detail below, the cavity 110A is further adapted to mechanically engage the inner shaft 116. The eyelet 110B extends transversely through opposing sides of the anchor tip 110 and is dimensioned for receipt of a suture. As illustrated in FIG. 1, the eyelet 110B is further positioned distally of the cavity 110A, where the longitudinal extent of the cavity 110A terminates proximal to the eyelet 110B and the cavity 110A does not intersect the eyelet 110B. As further discussed below, such configuration inhibits interaction of the anchor inserter 104 (e.g., the inner shaft 116) with a suture positioned within the eyelet 110B. However, in alternative embodiments, the cavity may be connected with the eyelet.

With regards to the anchor inserter 104, the outer shaft 114 is generally elongated and tubular. The inner shaft 116 also elongated, extending between proximal and a distal ends, and slidably received within both the outer shaft 114. Although not shown, in certain embodiments, the anchor inserter includes a handle at a proximal end, engaged to respective proximal ends of each of the outer and inner shafts, allowing a user grasping the handle to manipulate the position of the anchor inserter and a suture anchor mounted to the distal end thereof.

The inner shaft 116 is further adapted to move independently of the outer shaft 114. For example, the proximal end of the inner shaft may communicate with a user-actuatable mechanism, such as a trigger, allowing the inner shaft to be extended distally or retracted proximally with respect to the outer shaft. In further embodiments, not shown, the proximal end of the inner shaft may engage a rotatable element (e.g., a wheel, knob, etc.) mounted to the handle for rotation of the inner shaft with respect to the outer shaft.

The inner shaft and outer shaft of the anchor inserter may be formed from any materials capable of performing the functions of the anchor inserter. Examples of such materials include, but are not limited to, plastics, metals, and composites. In further embodiments, the anchor inserter may be formed from biocompatible materials.

Figure 1:
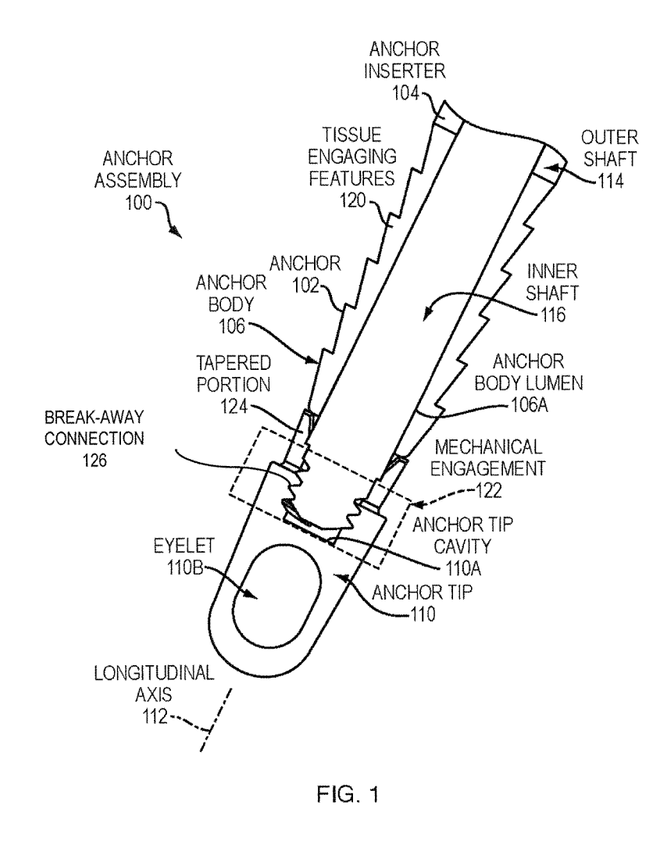
FIG. 1 is a schematic illustration of an embodiment of a suture anchor assembly including a two piece knotless suture anchor and corresponding anchor inserter, depicted in a cut-away side view.

FIG. 1 further illustrates the anchor 102 mounted to the anchor inserter 104 prior to use. The inner shaft 116 extends through the outer shaft 114 and the anchor body lumen 106A. The anchor tip 110 is positioned distally of the anchor body 106 and receives the distal end of the inner shaft 116 within the cavity 110A. In the embodiment illustrated in FIG. 1, the proximal end of the anchor body 106 is placed into contact with the distal end of the outer shaft 114 and the proximal end of the anchor tip 110 is placed into contact with the distal end of the anchor body 106. However, in alternative embodiments, a gap may be present between at least one of the proximal end of the anchor body and the distal end of the outer shaft and the proximal end of the anchor tip and the distal end of the anchor body.

The distal end of the inner shaft 116 and the anchor tip 110 are also adapted for engagement to each other (e.g., via mechanical engagement 122) when the anchor 102 is mounted to the anchor inserter 104. For example, the distal end of the inner shaft 116 and the cavity 110A are each formed with mating engagement features. As illustrated in the embodiment of FIG. 1, the mechanical engagement 122 is a threaded fastening including a first plurality of threads formed along an inner surface of the cavity 110A and a second plurality of threads formed along an outer surface of the distal end of the inner shaft 116. The first and second plurality of threads are adapted to mate with one another when the distal end of the inner shaft 116 is inserted within the cavity 110A and rotated. The threads are disengaged from one another by unthreading the distal end of the inner shaft 116 from the cavity 110A.

In further embodiments, the mechanical engagement may be a break-away or frangible connection 126, where the anchor tip 110 and distal end of the inner shaft 116 are disengaged from one another by breaking the mechanical engagement 122. For example, in the embodiment of FIG. 1, the first and second plurality of threads may be adapted to disengage from each other by stripping open. The inner shaft 116 is proximally retracted by a distance sufficient to shear at least one of the first and second plurality of threads, allowing the first and second plurality of threads to slip past one another. In another example, the first and second plurality of threads may be adapted to disengage from one another by unscrewing the inner shaft 116 with respect to the anchor tip 110.

In alternative embodiments, the mechanical engagement may adopt other forms and, optionally, mechanisms for providing breakaway functionality, as necessary. Examples may include, but are not limited to, mechanical stops such as mating protrusions and sockets, frictional engagements (e.g., press-fits), thermo-press fit/heat stake, snap fit, thinned wall sections, and the like.

Figure 2A:
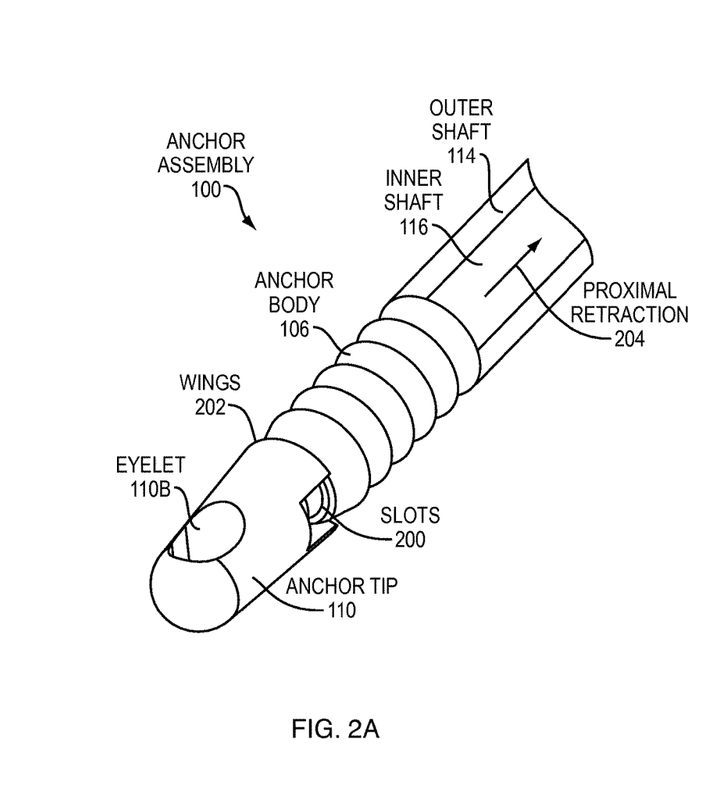
FIGS. 2A-2B are schematic illustrations of the anchor assembly of FIG. 1; (A) unactuated state; (B) actuated state.
Figure 2B:
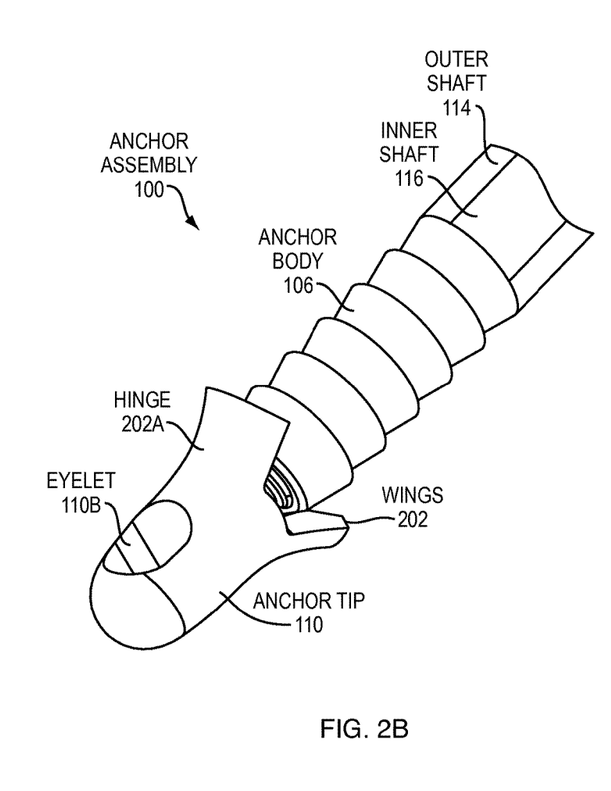

With further reference to FIGS. 2A-2B, the anchor assembly 100 is illustrated during use. A suture (not shown) is positioned within the eyelet 110B, where one or more free limbs of the suture extend outward from the eyelet 110B. After the suture is positioned within the eyelet 110B, at least a portion of the anchor 102 is inserted into a pre-formed bone hole within the patient's anatomy (not shown) using the anchor inserter 104. For example, the entire anchor may be inserted into the bone hole by pound in force directed to the anchor through the anchor inserter. During this insertion process, at least one of the free suture limbs is positioned so as to be impinged between the anchor body and the walls of the bone hole.

Beneficially, as discussed above, the anchor 102 is supported by the inner shaft 116, providing mechanical durability that allows the surgeon to move soft tissue and/or bone with the anchor assembly 100. In another example, the anchor tip 110 is useable by a surgeon as a probe to tactilely identify the location of the bone hole.

Until inserted into the bone hole, the components of the anchor assembly 100 do not substantially move relative to one another. This is accomplished by the mechanical engagement 122, which secures the anchor tip 110 to the inner shaft 116 and, in turn, constrains axial motion of the anchor body 106. However, once the anchor assembly 100 has been placed in the bone hole, the inner shaft 116 is retracted proximally (arrow 204) with respect to the anchor body 106 and outer shaft 114. Owing to the engagement between the anchor tip 110 and the inner shaft 116 provided by the mechanical engagement 122, the anchor tip 110 also moves proximally in response to this motion, causing the proximal end of the anchor tip 110 to be urged against the distal end of the anchor body 106.

The anchor tip 110 and the anchor body 106 are configured such that, when the proximal end of the anchor tip 110 is urged against the distal end of the anchor body 106, the proximal end of the anchor tip 110 deforms to accommodate receipt of at least a portion of the distal end of the anchor body 106 within the cavity 110A. Concurrently, the distal end of the anchor body 106 exhibits little to no deformation.

For example, in one embodiment, illustrated in FIGS. 2A-2B, the geometric shape of the anchor tip 110 provides the desired deformation in the proximal end of the anchor tip 110. The anchor tip 110 includes two slots 200 extending distally from its proximal end. In alternative embodiments, not shown, different numbers of slots may be present (e.g., one, three four, etc.). The slots 200 define a plurality of wings 202 there-between. When urging the proximal end of the anchor tip 110 against the distal end of the anchor body 106 (FIG. 2A), the wings 202 deflect outwardly from the anchor 100 (FIG. 2B), bending at hinge 202A.

As further shown in FIG. 1, embodiments of the anchor 100 may also include a tapered portion 124 on an inner surface of the cavity 110A. The tapered portion 124 narrows in thickness towards the proximal terminus of the anchor tip 110, widening the diameter of the cavity 110A towards the proximal terminus of the anchor tip 110. This configuration improves the ease with which the proximal end of the anchor tip 110 deforms to accommodate the portion of the distal end of the anchor body 106 received within the cavity 110A. It may be understood, however, that the tapered portion may be omitted in certain embodiments.

In another embodiment, the material from which the anchor tip and the anchor body are formed facilitate deformation of the proximal end of the anchor tip. For example, at least the proximal end of the anchor tip may be formed from a material that substantially deforms, elastically or plastically, when urging the proximal end of the anchor tip against the distal end of the anchor body. In one embodiment, the anchor tip may be more flexible than the anchor body. For example, the anchor tip may be formed from a first material (e.g., a polymer, metal, metal alloy, etc) while the anchor body is formed from second, stiffer material (e.g., a stiffer polymer, metal, metal alloy, etc.). In an embodiment, the proximal end of the anchor tip deforms radially outward to circumferentially overlie the portion of the distal end of the anchor body received within the cavity. Embodiments of the suture anchor assembly may employ such materials alone or in combination with one or more of the geometric features discussed above to facilitate deformation of the proximal end of the anchor tip to accommodate receipt of at least a portion of the distal end of the anchor body within the cavity.

Figure 3A:
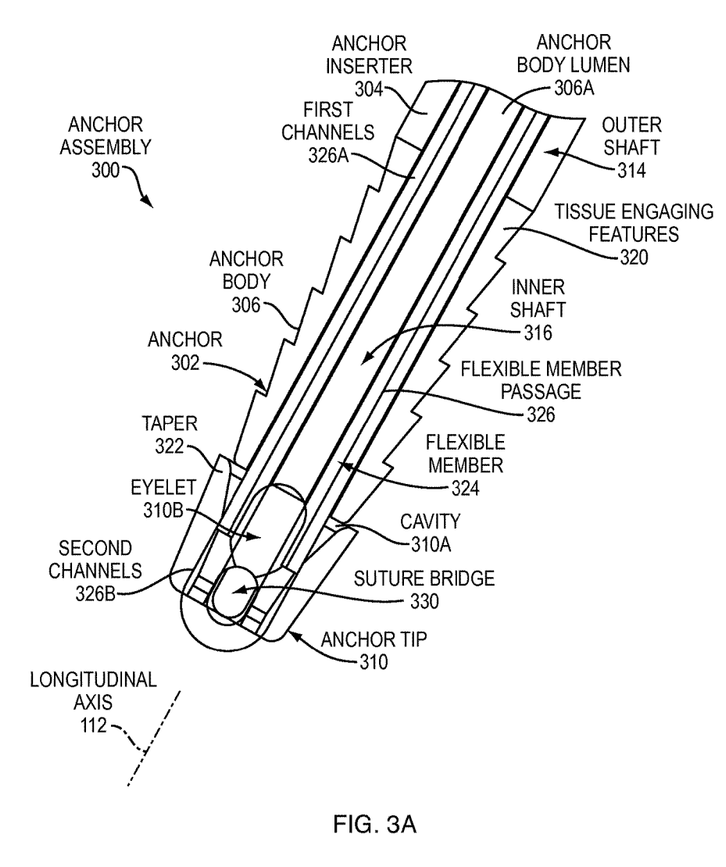
FIG. 3A is a schematic illustration of another embodiment of a suture anchor assembly including a two piece knotless suture anchor and corresponding anchor inserter, depicted in cut-away side view.
Figure 3B:
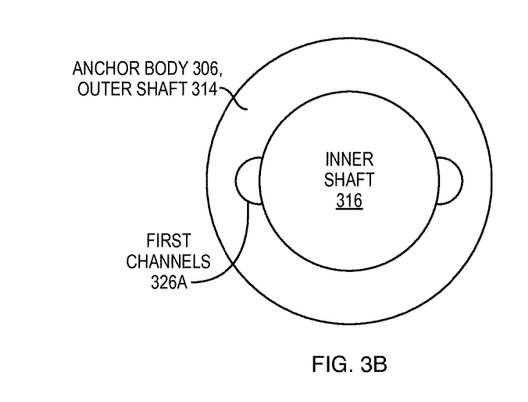
FIG. 3B is a schematic illustration of the anchor assembly of FIG. 3A in a transverse cross-sectional view.

FIGS. 3A-3B illustrate a second embodiment of the suture anchor assembly 300. Similar to anchor assembly 100, the anchor assembly 300 includes an anchor 302 and an anchor inserter 304, where the anchor includes an anchor body 306 and anchor tip 310 and the anchor inserter 304 includes an inner shaft 316 and an outer shaft 314. However, as discussed in detail below, the anchor assembly 300 further includes a flexible member 324 to constrain the anchor tip 310 in place with respect to the anchor body 306 during insertion and to proximally retract the anchor tip 310 into engagement with the anchor body 306. In certain embodiments, the flexible member 324 is a suture. However, in alternative embodiments, the flexible member 324 may include, but is not limited to, fishing string, wires (e.g., plastic, metal), springs, and the like.

With regards to the anchor 302, the anchor body 306 is generally tubular, including a lumen 306A extending along a longitudinal axis 312 between a proximal end and a distal end. In the embodiment of FIG. 3A, the anchor body 306 further includes a plurality of tissue engaging features 320 (e.g., a plurality of annular ribs) formed on an outer surface of the anchor body 306 for aiding fixation of the anchor within bone. However, in alternative embodiments, the tissue engaging features may include one or more of barbs, protrusions, threads, and the like. In further embodiments, the tissue engaging features may be omitted.

The anchor tip 310 is formed as a separate component from the anchor body 306 and includes a cavity 310A and an eyelet 310B. The cavity 310A is formed within the proximal end of the anchor tip 310 and extends distally there-from. The eyelet 310B extends transversely through the anchor tip 310 and is dimensioned for receipt of a suture (e.g., a repair suture 404, as discussed below). For example, as illustrated in FIG. 3A, the cavity 310A and eyelet 310B intersect, with the sidewalls of the eyelet 310B including a taper 322 that narrows moving towards the proximal end of the anchor tip 310. This taper 322 facilitates deformation of the proximal end of the anchor tip 310 when urged against the distal end of the anchor body 306, as discussed below. In further embodiments, the taper may be omitted.

With regards to the anchor inserter 304, the outer shaft 314 is generally elongated and tubular. The inner shaft 316 also elongated, extending between proximal and a distal ends, and slidably received within both the outer shaft 314. Although not shown, in certain embodiments, the anchor inserter includes a handle at a proximal end, engaged to respective proximal ends of each of the outer and inner shafts, allowing a user grasping the handle to manipulate the position of the anchor inserter and a suture anchor attached to the distal end thereof.

The inner shaft 316 is further adapted to move independently of the outer shaft 314. For example, the proximal end of the inner shaft may communicate with a user-actuatable mechanism, such as a trigger, allowing the inner shaft to be extended distally or retracted proximally with respect to the outer shaft. In further embodiments, not shown, the proximal end of the inner shaft may engage a rotatable element (e.g., a wheel, knob, etc.) mounted to the handle for rotation of the inner shaft with respect to the outer shaft.

Embodiments of the inner shaft and outer shaft of the anchor inserter may be formed from any materials capable of performing the functions of the anchor inserter. Examples of such materials include, but are not limited to, plastics, metals, and composites. In further embodiments, the anchor inserter may be formed from biocompatible materials.

In an embodiment, the anchor assembly 300 is further configured to accommodate at least a portion of the flexible member 324 therein. For example, as illustrated in FIG. 3A, the anchor assembly 300 includes a passageway 326 extending through the anchor inserter 304 and the anchor tip 310. The passageway 326 includes a first pair of longitudinal channels 326A, formed on respective inner surfaces of the anchor body lumen 306A and outer shaft 314, extending from the anchor inserter 304 to the distal end of the anchor body 306. The channels 326A are further aligned with complementary second pair of longitudinal channels 326B of the passageway 326 that are formed within the anchor tip 310 and extend from the proximal end to the distal end of the anchor tip 310.

The anchor tip 310 further includes a suture bridge 330. In the illustrated embodiment of FIG. 3A, the bridge 310 is interposed between longitudinal channels 326B and positioned at about the distal terminus of the anchor tip 310. When the flexible member 324 is routed through the anchor assembly 300, it is bent around the suture bridge 330, with the free limbs of the flexible member 324 extend proximally there-from, slidably received within the channels 326A, 326B.

Figure 3C:
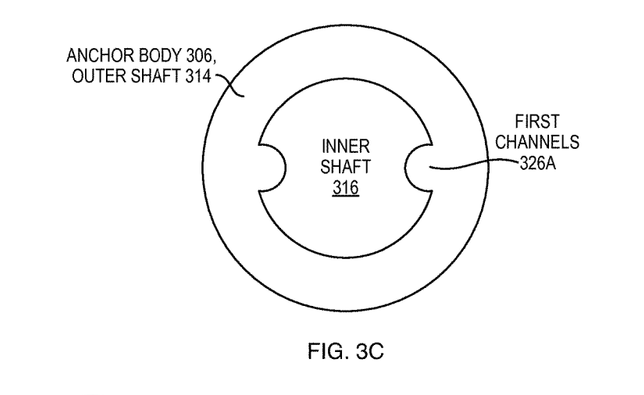
FIGS. 3C-3D are schematic illustrations of alternative embodiments of the anchor assembly of FIG. 3A in a transverse cross-sectional view.
Figure 3D:
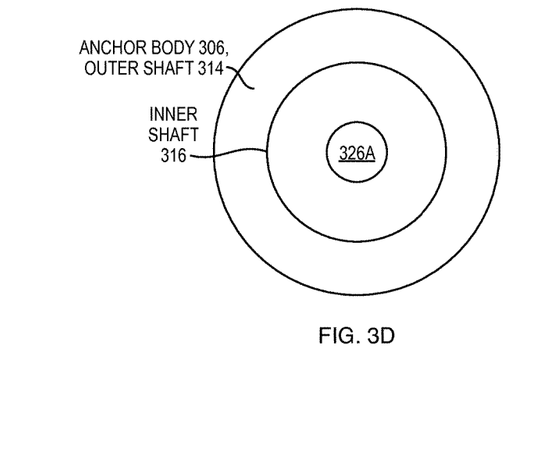

In alternative embodiments, the configuration of the passageway 326 may be modified. In one example, the configuration of the first channels 326A may be changed, with the first channels 326A may formed on an outer surface of the inner shaft 316 (FIG. 3C) or within the inner shaft 316. In another example, the first channels 326A may be formed as a single channel within the inner shaft 316 (FIG. 3D).

In further embodiments, the configuration of the second channels within the anchor tip may be changed to completely hide the flexible member within the anchor assembly, rather than routing the flexible member outside the distal end of the anchor tip. For example, the suture bridge may be offset from the distal terminus of the anchor tip by a selected distance. The passageway may further include a transverse segment within the anchor tip, distal to the suture bridge and intersecting the pair of channels, recessing the bent portion of the flexible member within the anchor tip.

FIG. 3A further illustrates the anchor 302 mounted to the anchor inserter 304 prior to use. The inner shaft 316 extends through the outer shaft 314 and the anchor body lumen 306A. The anchor tip 310 is positioned distally of the anchor body 306 and the flexible member 324 is routed through the passageway 326. In the embodiment of FIG. 3A, the proximal end of the anchor body 306 is placed into contact with the distal end of the outer shaft 314 and the proximal end of the anchor tip 310 is placed into contact with the distal end of the anchor body 306. However, in alternative embodiments, a gap may be present between at least one of the proximal end of the anchor body and the distal end of the outer shaft and the proximal end of the anchor tip and the distal end of the anchor body.

In certain embodiments, the engagement mechanism of FIG. 1 discussed above is omitted in the anchor assembly of FIG. 3A and, thus, the distal end of the inner shaft does not mechanically engage the anchor tip. In other embodiments, the engagement mechanism of FIG. 1 may be included in the anchor assembly of FIG. 3A and work in conjunction with the flexible member to proximally retract the anchor tip.

Figure 4A:
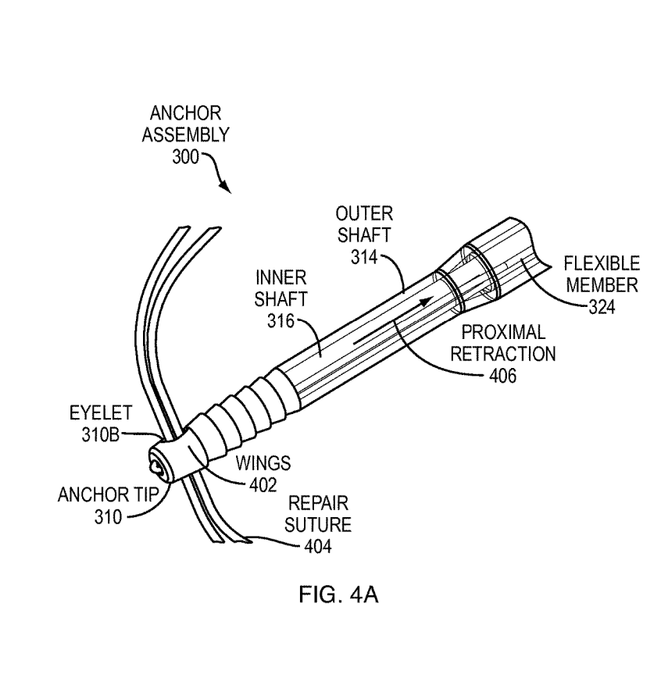
FIGS. 4A-4B are schematic illustrations of the anchor assembly of FIG. 3A; (A) unactuated state; (B) actuated state.
Figure 4B:
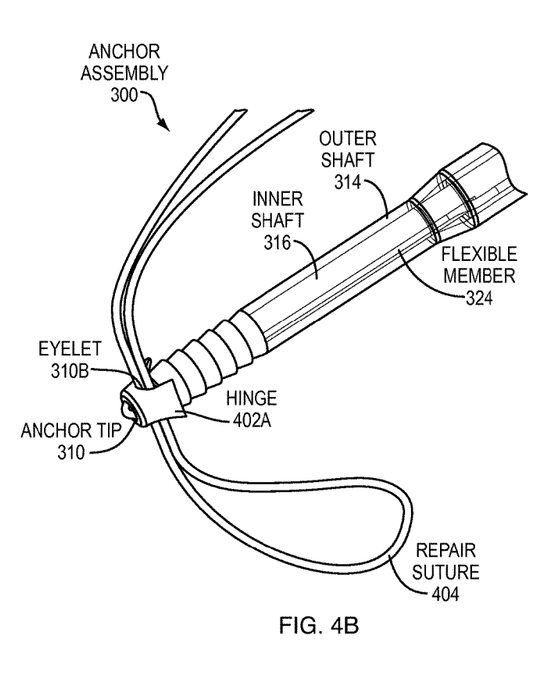

With further reference to FIGS. 4A-4B, the anchor assembly 300 is illustrated during use. A repair suture 404 is routed through the eyelet 310B, where or more free limbs of the repair suture 404 extend outward from the eyelet 310B. After the suture is positioned within the eyelet 310B, at least a portion of the anchor 302 is inserted into a pre-formed bone hole within the patient's anatomy (not shown) using the anchor inserter 304. For example, the entire anchor may be inserted into the bone hole by pound in force directed to the anchor through the anchor inserter. During this insertion process, at least one of the free limbs of the repair suture are positioned such that they are impinged between the anchor body and the walls of the bone hole. Similar to anchor assembly 100, the anchor 302 is supported by the inner shaft 316, providing mechanical durability that allows the surgeon to move soft tissue and/or bone with the anchor assembly 300. Furthermore, the anchor tip 310 is useable by a surgeon as a probe to tactilely identify the location of the bone hole.

Until inserted into the bone hole, the components of the anchor assembly 300 do not substantially move relative to one another. This is accomplished by maintaining a light tension (proximally) on the free limbs of the flexible member 324, sufficient to constrain axial motion of the anchor tip 310 and, in turn, the anchor body 306, but not sufficient to proximally actuate the flexible member 324 with respect to the anchor body 306. However, once the anchor assembly 300 has been placed in the bone hole, the flexible member 324 is proximally actuated, as illustrated by arrow 406. As the flexible member 324 is routed distally around the suture bridge 330, the anchor tip 310 also moves proximally in response to this motion. Initially, any gaps between the anchor tip, the anchor body, and the outer shaft are closed. Subsequently, the proximal end of the anchor tip is urged against the distal end of the anchor body.

For example, in an embodiment (not shown), the proximal end of the flexible member is routed through a handle of the anchor inserter. This allows a user grasping the handle to proximally retract the flexible member.

As discussed above in regards to anchor assembly 100, the anchor tip 310 and the anchor body 306 are configured such that, when the proximal end of the anchor tip 310 is urged against the distal end of the anchor body 306, the proximal end of the anchor tip 310 deforms to accommodate receipt of at least a portion of the distal end of the anchor body 306 within the cavity 310A. Concurrently, the distal end of the anchor body 306 exhibits little to no deformation.

For example, as illustrated in FIGS. 4A-4B, the eyelet 310B may define geometric features such as wings 402 that deform about a hinge 402A and/or a taper 322 in the proximal end of the anchor tip 310. Alternatively or additionally, at least the proximal end of the anchor tip is formed from a material that substantially deforms, elastically or plastically, when urging the proximal end of the anchor tip against the distal end of the anchor body.

In addition to the primary fixation between the anchor body 306 and the walls of the bone hole, as discussed above, the anchor assembly 300 also provides a secondary point of fixation between the anchor 302 and the repair suture 404. Notably, the repair suture 404 is impinged between the proximal end of the anchor tip 310 and the distal end of the anchor body 306.

In certain embodiments, the anchor assemblies 100, 300 may be provided as a kit, including the anchor and the anchor inserter pre-assembled. Such a configuration is beneficial for completely disposable systems, where the anchor inserter is discarded after being used to insert the attached anchor. In alternative embodiments, the anchor and anchor inserter may be provided separately and subsequently assembled. Such a configuration is beneficial for partially reusable systems, where the anchor inserter is saved and reconditioned for further use after being employed to insert an anchor that has been attached thereto.

The terms comprise, include, and/or plural forms of each are open ended and include the listed parts and can include additional parts that are not listed. The term and/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:
1. A suture anchor assembly, comprising:
 a suture anchor, comprising:
  an elongated anchor body having a lumen extending there-through between a proximal end and a distal end along a longitudinal axis; and
  an anchor tip having a proximal end and a distal end, the anchor tip and including an eyelet extending transversely there-through and a cavity formed in the proximal end of the anchor tip, wherein the proximal end of the anchor tip does not extend into the anchor body lumen, wherein the cavity does not intersect the eyelet, and wherein the tip is separate from of the anchor body; and
 an anchor inserter, comprising:
  a tubular outer shaft extending between a proximal end and a distal end; and
  an inner shaft slidably receivable within the outer shaft and the anchor body lumen
 wherein the distal end of the inner shaft is mechanically engageable with the cavity of the anchor tip so as to position the anchor tip distally of the anchor body;

wherein the inner shaft is proximally retractable while mechanically engaged with the anchor tip so as to urge the proximal end of the anchor tip against the distal end of the anchor body; and wherein the proximal end of the anchor tip is deformable to accommodate receipt of at least a portion of the distal end of the anchor body within the cavity upon being urged proximally against the distal end of the anchor body.

2. The suture anchor assembly of claim 1, wherein the proximal end of the anchor tip deforms radially outward to circumferentially overlie the portion of the distal end of the anchor body received within the cavity.

3. The suture anchor assembly of claim 1, wherein the anchor tip further comprises a plurality of slots extending distally from the proximal end of the anchor tip along the length of the cavity defining a plurality of wings and wherein the plurality of wings deflect outward to accommodate the portion of the distal end of the anchor body received within the cavity.

4. The suture anchor assembly of claim 1, wherein a diameter of the cavity at the proximal end of the anchor tip is less than a diameter of the distal end of the anchor body.

5. The suture anchor assembly of claim 4, wherein the inner shaft does not engage the suture.

6. The suture anchor assembly of claim 1, wherein the mechanical engagement between the distal end of the inner shaft and the cavity is a break-away connection.

7. The suture anchor assembly of claim 6, further comprising:
   a first plurality of threads formed along an inner surface of the cavity; and
   a second plurality of threads extending proximally from the distal end of the inner shaft, the second plurality of threads adapted to mate with the first plurality of threads;
   wherein the first and second plurality of threads are disengageable from one another by stripping upon proximal retraction of the inner shaft with respect to the inner shaft by a distance sufficient to shear at least one of the first and second plurality of threads and allow the first and second plurality of threads to slip past one another.

8. The suture anchor assembly of claim 1, further comprising a suture extending through the eyelet.

9. The suture anchor assembly of claim 1, wherein the tip is comprised of a first material and the body is comprised of a second material different than the first material, and wherein the second material is selected to be harder than the first material.

10. The suture anchor assembly of claim 9, wherein the first material is selected to be elastically or plastically deformable.

* * * * *